United States Patent [19]
Falknor

[11] Patent Number: 5,246,428
[45] Date of Patent: Sep. 21, 1993

[54] NEEDLE SAFETY MECHANISM

[76] Inventor: Donald W. Falknor, 66 Heathrow, Sugarland, Tex. 77479

[21] Appl. No.: 922,568

[22] Filed: Jul. 30, 1992

[51] Int. Cl.$^5$ .............................................. A61M 5/00
[52] U.S. Cl. .................................... 604/198; 604/263
[58] Field of Search ............... 604/195, 198, 192, 187, 604/110, 263

[56] References Cited

U.S. PATENT DOCUMENTS

| | | |
|---|---|---|
| 4,507,118 | 3/1985 | Dent .................................... 604/198 |
| 4,664,654 | 5/1987 | Strauss . |
| 4,894,055 | 1/1990 | Sudnek . |
| 4,900,311 | 2/1990 | Stern et al. . |
| 4,923,447 | 5/1990 | Morgan . |
| 4,946,446 | 8/1990 | Vadher . |
| 4,966,592 | 10/1990 | Burns et al. . |
| 4,973,316 | 11/1990 | Dysarz . |
| 5,013,301 | 5/1991 | Marotta, Jr. et al. . |
| 5,104,385 | 4/1992 | Huband ................................. 604/198 |

Primary Examiner—John D. Yasko
Attorney, Agent, or Firm—Browning, Bushman, Anderson & Brookhart

[57] ABSTRACT

A safety mechanism for a hypodermic needle comprises a base adapted to be fixed with respect to the needle and a tubular sheath mounted for relative longitudinal movement with respect to the base between a first position for covering the needle and a second position wherein the needle can at least partially protrude from the outer end of the sheath. A latch mechanism cooperative between the base and the sheath is selectively repeatedly shiftable between a latching mode wherein the sheath is latched in its first position, and a free mode wherein the sheath is reciprocable between its first and second positions, the latch including detents for releasably retaining the latch in its free mode.

24 Claims, 3 Drawing Sheets

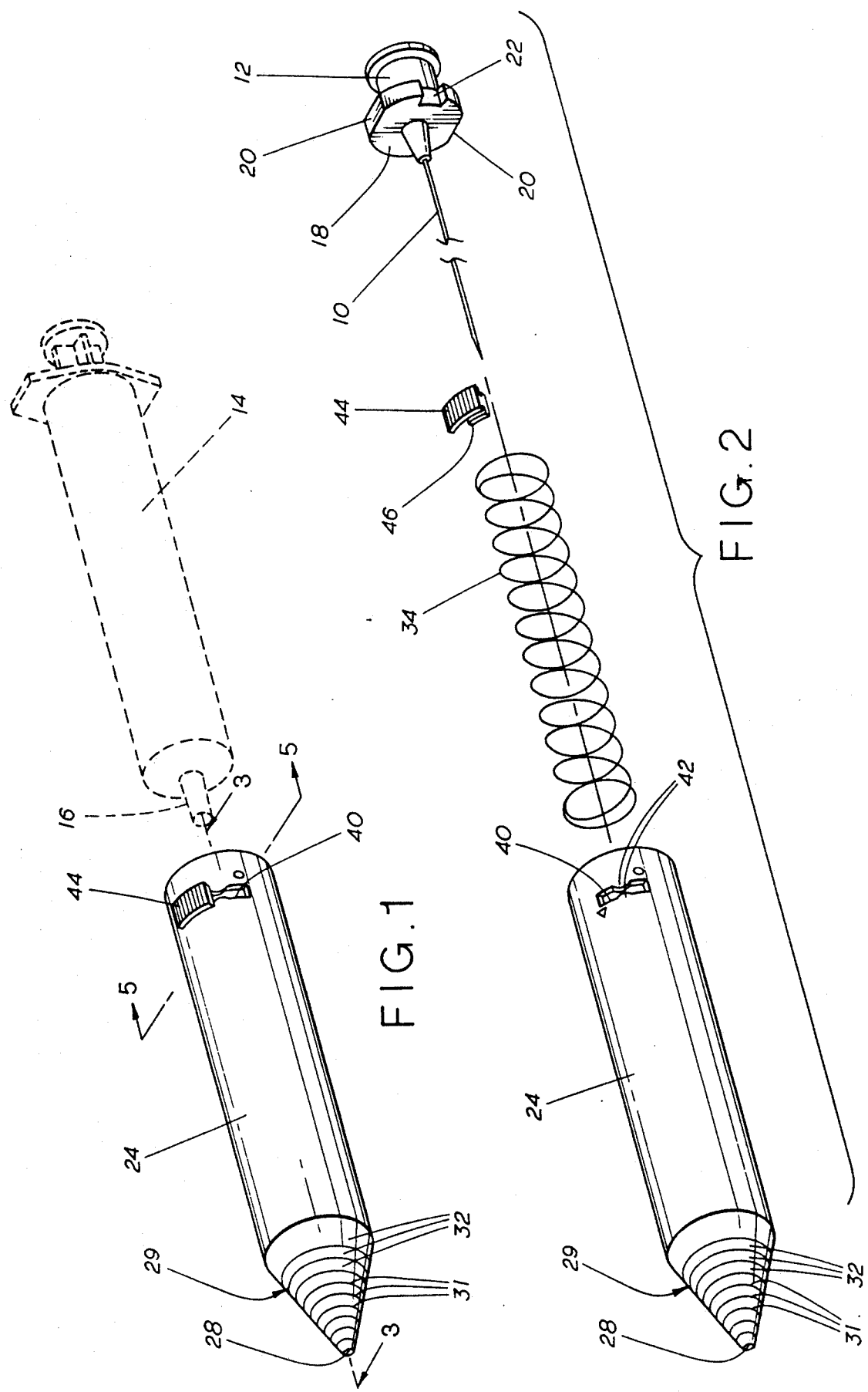

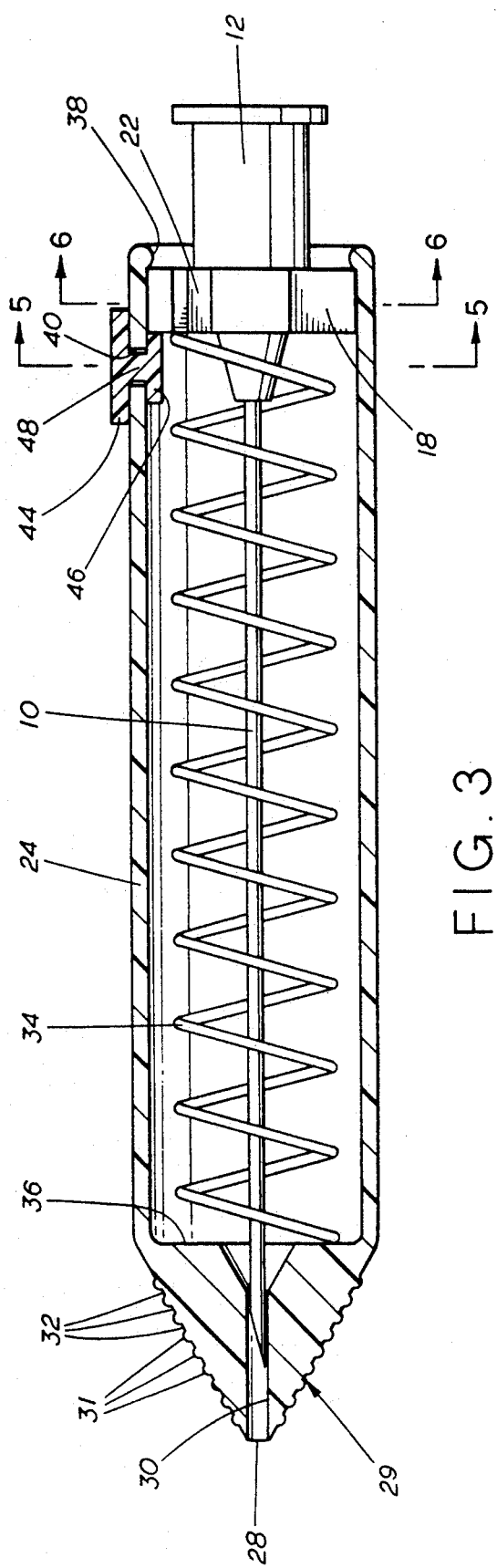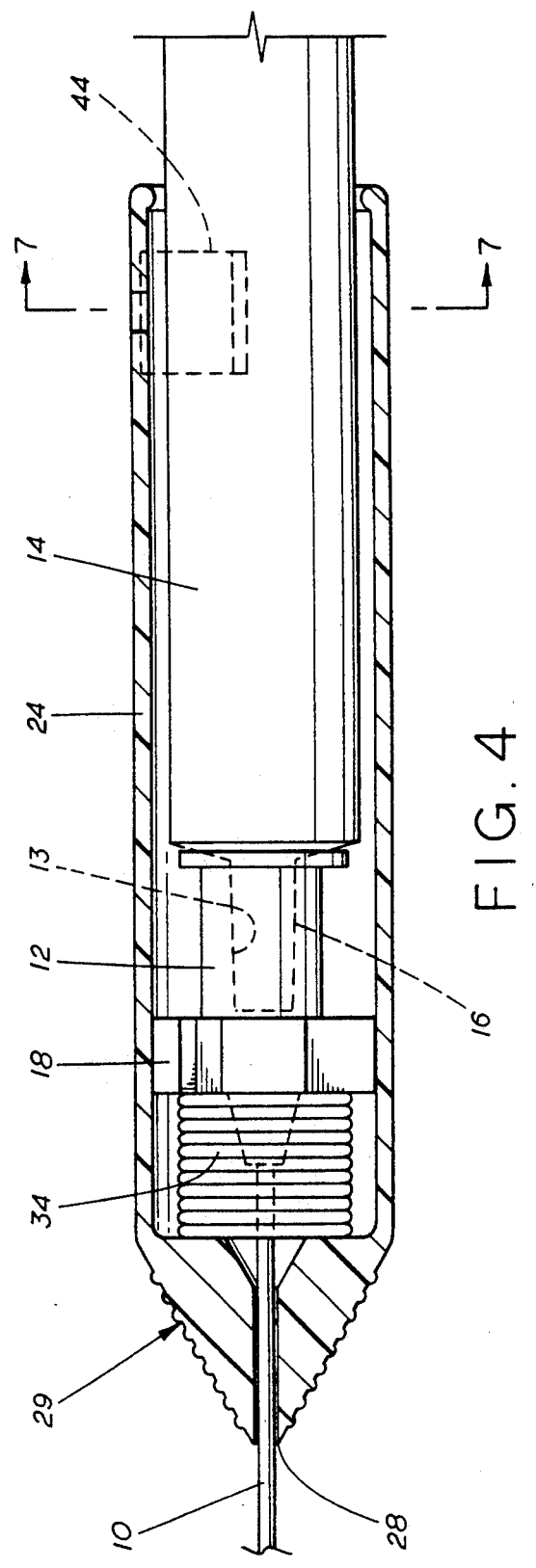

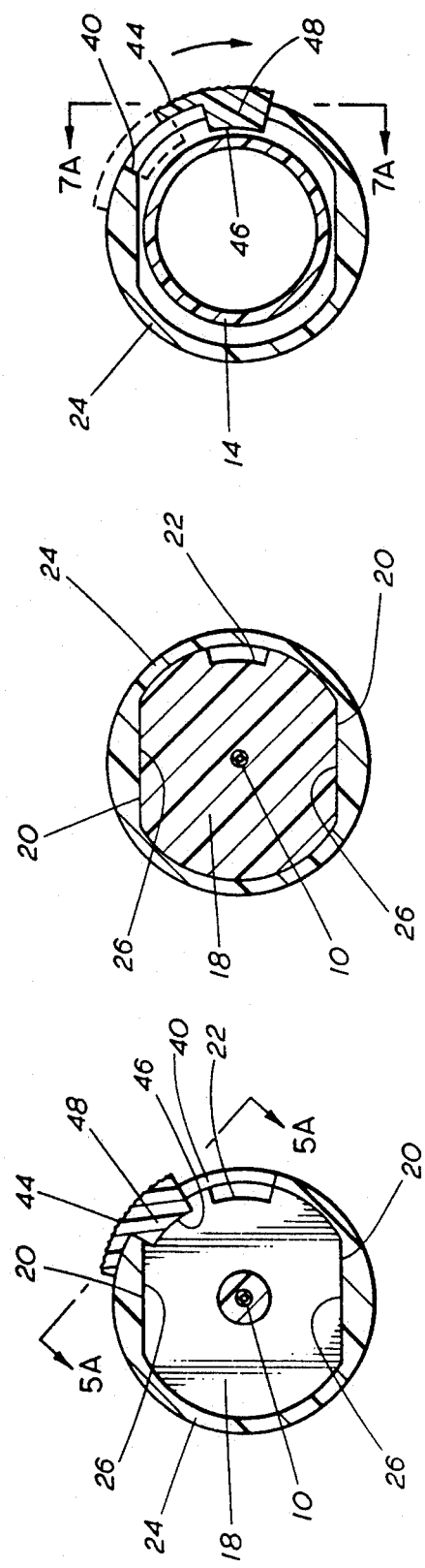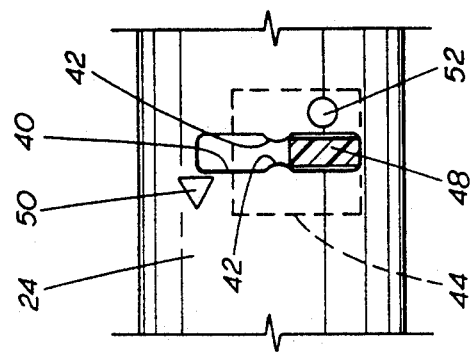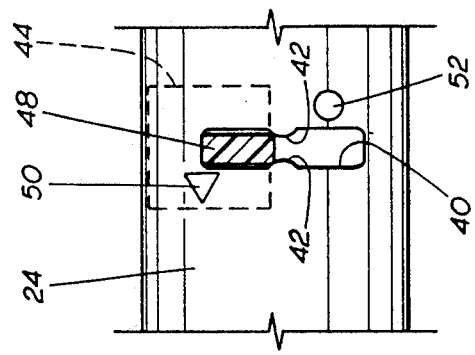

NEEDLE SAFETY MECHANISM

BACKGROUND OF THE INVENTION

The present invention addresses the problem of accidental scratching of medical personnel and/or laboratory personnel by hypodermic needles. This problem has become much more serious of late due to the increased presence of the HIV virus and other serious infectious microorganisms. The precautions now required of medical establishments regarding handling and disposal of needles are quite onerous, and even those do not eliminate accidental scratches and/or punctures.

Modern disposable needles are provided with removable and replaceable covers, which offer some protection, but the very acts of removing and replacing such a cover lend themselves to the very kind of accident sought to be prevented. Also, it is a virtual necessity that the needle be left uncovered between filling of the syringe and giving the injection.

Accordingly, a number of efforts have been made, particularly in the last few years, to develop safety mechanisms which can be associated with needles and/or syringes to further reduce the risk. Many of these efforts have involved designs for protective sheaths which can be attached to a needle or a syringe to cover the needle after and/or before its use. However, many of these are relatively bothersome to use and/or do not, respectively, cover the needle and permit uncovering of the needle at all appropriate times.

U.S. Pat. No. 4,664,654 to Strauss and U.S. Pat. No. 4,900,311 to Stern et al. disclose such sheaths. However, both of them require the sheath to be retracted, so as to uncover the needle, and latched into a retracted position prior to using the needle, i.e. inserting it into a vial to take in medication and/or injecting it into a patient. This is unsatisfactory because it is just prior to, during, and immediately after such procedures that the accidental scratches and/or punctures are most likely to occur.

The device disclosed is U.S. Pat. No. 4,973,316 to Dysarz likewise leaves the needle uncovered prior to use, and the pushing of the plunger of the syringe releases a sheath so that it will automatically be extended to cover the needle as that needle is removed from the patient's body. Moreover, since the latch which holds the sheath retracted prior to pushing the plunger is only usable once, and the sheath, when it advances to cover the needle, becomes locked in its extended position, the needle can never be uncovered or used again without destroying the device. Thus, in addition to sharing the general problems above concerning Strauss and Stern et al., the Dysarz device could be triggered into its needle covering mode if the syringe plunger is pushed all the way in prior to taking up medication from a vial, whereupon the sheath would be permanently locked in place and the syringe could not be used to give the injection.

U.S. Pat. No. 4,894,055 to Sudnek does provide a sheath which remains in an extended, needle covering position until it is placed against the patient's body, and the needle projected beyond it and into the patient's body. However, as with Dysarz, as the needle is withdrawn from the patient's body, a spring extends the sheath over the needle and a permanent lock automatically locks the sheath in its extended position. Thus, like Dysarz, Sudnek presents problems in terms of being able to fill the syringe before giving the injection.

U.S. Pat. No. 4,923,447 to Morgan, U.S. Pat. No. 4,966,592 to Burns et al., and U.S. Pat. No. 5,013,301 to Marotta, Jr. et al., all describe devices intended to be operated in much the same manner as those of Strauss and Stern et al. in that it is intended that the sheath be unlatched from an extended position covering the needle, manually retracted, and latched into a retracted position prior to using the needle. If one were to attempt to thwart the prescribed use by unlatching the sheath from its extended position, but not manually retracting it, and attempt to use it somewhat in the manner described by Sudnek, a slight contact with the sheath could inadvertently re-latch the sheath in its extended position. Moreover, Morgan and Burns et al., are more complex structurally than is desirable for an inexpensive disposable syringe combination, and Marotta, Jr. et al., is bothersome in that a separate clip is completely removed to unlock the sheath and must be re-emplaced to relock the sheath in its extended position after use.

U.S. Pat. No. 4,946,446 to Vadher is even more complicated. Its structure and operation is a reminiscent of the sort of ballpoint writing pen in which successive longitudinal pushes on an actuator button or the like alternately extend and retract the writing tip of the pen from a casing. In Vadher, it is the needle which is successively extended and retracted. It is also noted that, whereas many of the prior art devices described above mount a sheath on a syringe. There are a number of reasons why it might be considered preferable to mount the sheath directly to the needle sub-assembly, and Vadher attempts to do this. However, it that context, i.e. in terms of a device intended to be mounted on a needle sub-assembly, the mechanical complexity of Vadher, and most especially the lengthwise dimension required for the working parts, is particularly undesirable and unpractical.

A device known as the "3 cc. Safety-Lok Safety Syringe" and available from Becton Dickinson is believed to be similar to Sudnek and Dysarz in that a sheath which can be advanced to cover a needle after use is then permanently locked in place so that the needle cannot be re-used.

Another commercial system known as the "Monoject System of Safety" and available from Sherwood Medical of Saint Louis Missouri simply provides a large sheath which can be removed from the needle prior to filling and then used as part of a stand in which the needle can be placed until the injection is given, whereafter the sheath is again used to cover the needle for disposal.

SUMMARY OF THE INVENTION

The present invention provides a safety mechanism for a hypodermic needle. The mechanism includes a base member adapted to be fixed with respect to the needle and a tubular sheath member mounted for relative longitudinal reciprocation with respect to the base member. In one preferred embodiment, the base member is, or is incorporated in a fitting which mounts the needle at one end and has the other end adapted for connection to a syringe. The sheath member is reciprocable between a first or extended position, in which it covers the needle, and a second or retracted position, wherein the needle at least partially protrudes from an outer end of the sheath member. It should be understood that the reciprocating movements are relative, as are the first and second positions, so that the first position might also be considered a retracted position of the needle, and the second position might be considered an extended position of the needle.

A latch means, cooperative between the base and sheath members, is selectively repeatedly shiftable between a latching mode, wherein the sheath is latched in its first position, and a free mode, wherein the sheath member is reciprocable between its two positions, as described above.

Accordingly, and unlike many of the prior art devices described above, the mechanism of the present invention can be unlatched, so that the sheath is free for potential retraction but can remain in its extended or first position until the very moment that the needle is to be inserted into a vial or injected into a patient. Indeed, there is no need to manually retract the sheath. The operator simply brings the outer end of the sheath into contact with the vial or the patient's body and then continues pushing on the barrel of the syringe as if using an ordinary unsheathed device. The abutment of the outer end of the sheath with the vial or the body will cost the sheath to be "retracted" with respect to the needle (literally restrained against further movement so that the needle can be extended out through an opening in the outer end of the sheath).

A spring is preferably provided, cooperative between the base and sheath members, to bias the sheath to its first, extended, or needle covering position, so that as the needle is withdrawn from the vial or the patient, the sheath automatically progressively covers it. The needle literally need never be uncovered or exposed except when it is in the vial or in the patient. Stop means cooperative between the sheath and base members limit the movement of the sheath member to its extended position under influence of the spring, i.e. prevent the sheath member from being pushed or falling off of the base member.

In preferred embodiments, the latch means permits of a simple one handed operation which can be performed very shortly before injecting the needle into a vial or patient, and can even be performed after the outer end of the sheath has already been in contact with the vial or the patient. Furthermore, because of the spring, even if the latch is released slightly before contacting the vial or the patient with the end of the sheath, the sheath will not slip into its retracted position nor be moved to that position by a slight inadvertent touch against some other object.

Because the latch can be selectively and repeatedly latched and freed, it is possible not only to allow the needle to be recovered after drawing medicine from a vial and before giving the patient an injection (which, as mentioned, is automatically caused by the spring biasing), but it is even possible to positively latch the sheath in its extended position at that time, even further ensuring against accidents. Indeed, the sheath may be retracted and re-extended as many times as desired, e.g. if giving a patient a number of small injections of local anesthesia in the same general vicinity of the body. The sheath can be latched into its first position, after the injection has been given, for disposal of the needle and/or the needle/syringe combination.

Of course, the sheath and latch operates similarly, and equally effectively, if the needle is being used to aspirate blood or other bodily fluid from the patient rather to give an injection, and it is particularly noted that the action of the sheath and the latch are completely independent of the movements of the syringe plunger.

When the latch is shifted into its free (unlatched) mode, detent means releasably hold it in that mode so that it cannot be inadvertently re-latched by some slight movement or touch, and the sheath, though extended by the spring, remains free for potential retraction. It is preferable that these detent means also be operative to releasably retain the latch in its latching mode.

The sheath preferably has a slit therethrough, elongated in a circumferential sense, and the latch preferably includes a latch operator having an engagement portion accessible from the outside of the sheath, and a projection extending radially inwardly from the engagement portion through the slit. The slit is longer than the projection, so that the latch operator can be moved in a circumferential sense in the slit to effect the latching and free modes. When the latch operator is in the latching mode, with the projection located at one end of the slit, the projection is circumferentially offset from a radial notch in a flange on the base member, and thus axially opposes that flange. When the latch operator is shifted to the free mode, with the projection located at the other end of the slit in the sheath, the projection is circumferentially aligned with the notch in the base flange, and since it is sized to be received therein, the axial opposition between the projection and the flange is eliminated, and the sheath which carries the latch operator can reciprocate with respect to the base member.

Even more preferably, the aforementioned detent means may comprise a pair of small ear-like snap formations projecting laterally inwardly from the sides of the slit, approximately midway along its length. These are spaced apart by a distance slightly smaller than the like dimension of the portion of the operator projection which passes through the slit, so that they resist movement of the operator between the latching and free modes. However, the spacing is large enough, and either the snap formations and/or the latch operator projection sufficiently resilient, that the latch projection can be forced or snapped past these formations by application of sufficient force, in a circumferential sense, to the attached engagement portion of the latch operator.

It will be appreciated that, because this latch operator moves in a circumferential sense, and because of its manner of coaction with the flange on the base member, neither the latch operator nor the flange need have great longitudinal dimensions, and the system can easily be incorporated in a needle sub-assembly without undesirably increasing its length, bulk, or the like. Also, this form of latch is particularly simple, which imparts decided advantages both in terms of manufacture and use.

Because the preferred mode of operation involves abutment of the outer end of the sheath with the patient's body as the needle is being injected thereinto, use of the needle and syringe are facilitated if a portion of the external surface of the sheath near its outer end is tapered inwardly toward that end, e.g. in generally frustoconical configuration. This facilitates application to the patient's body, or to a vial, at any desired angle. Also, in order to resist slipping of the sheath against the patient's skin after it has been properly positioned, the tapered portion of the external surface of the sheath may be provided with surface irregularities, such as a series of alternating circumferential grooves and ridges.

Various objects, features and advantages of the invention will be made apparent by the following detailed description, the drawings, and the claims.

BRIEF DESCRIPTION OF THE DRAWINGS

FIG. 1 is a perspective view of an assembled device according to the invention in position for mounting on a standard syringe.

FIG. 2 is an exploded, perspective view of the device.

FIG. 3 is a longitudinal cross-sectional view through the device with the sheath extended and latched.

FIG. 4 is a view similar to that of FIG. 3 with the mechanism unlatched and the sheath retracted.

FIG. 5 is a transverse cross-sectional view taken on the line 5—5 of FIG. 3.

FIG. 5a is a detailed plan view taken on the line 5a—5a of FIG. 5 showing the "latched" indicator.

FIG. 6 is a transverse cross-sectional view taken on the line 6—6 of FIG. 3.

FIG. 7 is a transverse cross-sectional view taken on the line 7—7 of FIG. 4.

FIG. 7a is a detailed plan view taken on the line 7a—7a of FIG. 7 showing the "free" indicator.

DETAILED DESCRIPTION

The drawings depict a safety mechanism according to an exemplary preferred embodiment of the invention. In the embodiment shown, the safety mechanism is incorporated in a needle sub-assembly which includes a hypodermic needle 10 having a pointed free end and a base end mounted in a fitting 12. At the other end of fitting 12 is a longitudinal socket 13 which is adapted to be removably connected to the forward fitting 16 of a standard hypodermic syringe 14, in the manner well known in the art. Fitting 12 also serves as the base member of the safety mechanism. Near its forward end, the fitting 12 has a generally radially extending flange 18. (As used herein, terms such as "radial," "longitudinal," and "circumferential" will be with reference to the centerline of needle 10 unless otherwise noted.) The flange 18 is part circular, but with the circular configuration interrupted by diametrically opposite flats 20. On one side, midway between the flats 20, there is a radial notch 22.

The device further comprises a generally cylindrical sheath 24 surrounding flange 18 and mounted for longitudinal reciprocation with respect thereto. The major part of sheath 24 is straight-sided, and circular in external transverse configuration, its internal transverse configuration being part circular, but having built up flattened areas 26, so that it mates with the general configuration of plate 18, but for notch 22 (see FIG. 6). The inner dimension of the main portion of sheath 24, including its rear lip 38, is sized to clear the barrel 14 of a syringe of the size for which the particular assembly is designed. It will be appreciated that the main portion of the sheath 24 can be made as large as necessary in order to so clear the syringe, and plate 18 would be correspondingly sized.

Adjacent the forward or outer end 28, a portion 29 of the external surface of sheath 24 is tapered inwardly toward end 28 along a generally frustoconical locus. Portion 29 also has surface irregularities, specifically a series of coaxial ridges 31 and grooves 32 progressing longitudinally therealong. The interior portion of sheath 24 corresponding to external portion 29 has a reduced inner diameter 30 sized to slidingly receive, and therefore guide, needle 10.

A helical coil spring 34 is disposed within the main, large diameter, portion of the sheath 24 and in surrounding relation to the needle 10. The ends of spring 34 abut the flange 18 and the shoulder 36 formed between the large and small diameters to bias the sheath 24 to its first or extended position, as shown in FIGS. 1 and 3, in which the needle 10 is fully enclosed therein. An in-turned lip 38 on sheath 24 abuts the rear of plate 18, serving as a stop to limit the forward extension of sheath 24 and retain it on the assembly.

It can be seen that, if the sheath 24 is not latched with respect to the needle 10 and its fitting 12, spring 10 can compress, allowing the sheath 24 to retract relative to the needle 10 (or the needle 10 to advance relative to the sheath 24) so that an injection can be given. More specifically, if the sheath is unlatched, the assembly can simply be applied to the patient's skin, more or less in the same manner as a conventional needle, whereupon abutment of conical portion 29 with the body will stop forward movement of the sheath, while the needle 10 can continue forward movement and project through the end 28 of the sheath and into the body. The ridges and grooves 32 help to prevent the sheath from slipping on the patient's skin, while the conical or tapered external configuration of sheath portion 29 allows the needle to be applied at virtually any desired angle to the patient's body.

As the needle is withdrawn from the patient's body, the spring the 34 will automatically progressively return the sheath to its extended position covering the needle 10. The same action occurs when inserting/withdrawing the needle with respect to a vial. Thus, the only time the point of the needle 10 is exposed is when it is in the patient's body or the vial, so that there is virtually no chance of accidental scratching of other people, particularly since the sheath 24 can be latched in its extended position when desired.

To achieve this latching, but in a manner which is releasable, the rear portion of the sheath 24 is provided with a partial circumferential slit 40. A pair of small arcuate detent tabs or snap formations 42 project laterally (with reference to slit 40) inwardly toward each other from opposite sides of the slit 40. A latch operator has an engagement portion in the form of a knurled, arcuate outer plate 44 lying along the outside of sheath 24, in the vicinity of slit 40, and large enough to abut the sheath on opposite sides of slit 40. The operator also includes a projection extending radially inwardly from plate 44. The projection in turn includes a connecting element 48 disposed in slit 40 and an inner retainer plate 46 lying within the sheath 24, and long enough to abut the sheath on opposite sides of slit 40 and hold operator 44, 46, 48 in place. Connecting element 48 is sufficiently shorter than slit 40 to lie on one side or the other of snaps 42. Element 48 is large enough to abut snaps 42, so that it cannot slip past them, yet snaps 42 are sufficiently flexible to allow element 48 to be shifted past them by applying sufficient force to rotate operator 44, 46, 48 via outer plate 44.

The aforementioned notch 22 is sized to receive projection 46, 48. However, when the latch operator 44, 46 and 48 is in its latched mode (FIGS. 1, 5, and 5a), projection 46, 48 is circumferentially offset from notch 22 and opposes the plate 18, so that the sheath 24 carrying the operator 44, 46, 48 cannot move rearwardly with respect to plate 18, and thus the attached needle 10. Also in this latched mode, the outer plate 44 covers a "free" indicator 50 on the exterior of sheath 24, and exposes a "latched" indicator 52, also on the sheath 24. Indicator 50, for example, may be a green arrow pointing forward, while indicator 52 may be a red circle.

By circumferentially shifting operator 44, 46, 48 via its outer plate 44, element 48 can be forced past snaps 42 so that the operator moves to the "free" mode of FIGS. 4, 7 and 7a. It can be seen that, in this mode, the projection 46, 48 is aligned with notch 22, so that the attached sheath 24 can retract rearwardly with respect to needle 10 and its fitting 12. As shown in FIG. 7a, when the device is in free mode, plate 44 covers the latched indicator 52, and exposes the free indicator 50. Preferably, the device is only unlatched or freed just prior to filling the syringe and/or giving an injection (or invading the patient's body to draw a fluid sample), and is reattached immediately after each such procedure. This is easily done by simply using the thumb of the hand holding the syringe to apply the shifting force to plate 44.

When the use of the needle is finished, the entire assembly, still latched, can be removed from the syringe 14, in the same manner that an ordinary needle is removed from a standard syringe, and discarded.

A typical preferred operation could proceed as follows: The operator would receive the needle subassembly, which may or may not be pre-attached to barrel 14 of the syringe, but which would, in any event, be received with the sheath 24 in its first or extended position and the operator 44, 46, 48 in its latched mode. If the needle sub-assembly is not pre-emplaced on the syringe 14, the operator installs it there. It will be noted, with reference to FIG. 3, that the portion of fitting 12 which must co-act with the syringe 14 protrudes from sheath 24 when the latter is in its extended and latched condition, so that there is no interference with assembly to the syringe, whether done in advance at the manufacturing facility or done on site by the health care worker.

The worker, if preparing to give an injection, would swab the top of the medicine vial with alcohol, in the usual manner, shift the operator 44, 46, 48 to its free position, bring the end 28 of the sheath 24 to the top of the vial, holding the apparatus by the syringe barrel, and then continue to push inwardly on the syringe barrel. Abutment of sheath 24 with the top of the vial would prevent further movement of sheath 24, so that needle 10 will proceed outwardly or forwardly through end 28 and into the vial, and the medicine can be taken up in the usual manner by first advancing, then retracting, the syringe plunger. The sheath 24 is preferably formed of the transparent plastic material, so that, when it is in its second or retracted position, as shown in FIG. 4, the worker can still read the scale ordinarily printed on the syringe barrel 14.

After the syringe has been filled, the worker simply pulls the syringe barrel away from the vial, and as the needle 10 emerges from the vial, the spring 34 will automatically and progressively extend the sheath 24 over the needle 10, so that the needle 10 is never exposed. The worker can then shift operator 44, 46, 48 back to its latched mode so that the needle 10 cannot be accidently exposed. It will be understood that, if desired, end 28 and portion 29 of sheath 24 can be presterilized and covered with a cap similar to those provided on conventional disposable needle/syringe assemblies. However, if such a cap has not been provided, or if for any reason the worker believes the exterior of the sheath may have been contaminated, surface 29 and end 28 can be swabbed with alcohol without danger of retracting the sheath with the apparatus in its latched mode.

The worker can then prepare the patient, unlatch the mechanism via plate 44, and inject needle 10 into the patient's body in much the same manner that it was injected into the medicine vial. The conical overall configuration of portion 29 allows the needle to be applied to the patient at any desired angle, and the surface irregularities 31, 32 help to prevent sheath 24 from slipping on the patient's skin once it has been emplaced in a particular spot. This allows for accuracy of emplacement, minimizes the chance of accidents or discomfort to the patient, and also minimizes the need for sterilization of the exterior of portion 29 and end 28 of the sheath.

Once again, as the worker moves the syringe barrel 14 away from the patient's body, and the needle 10 gradually emerges, the spring 34 will progressively extend the sheath 34 over the needle 10. The mechanism can be promptly re-latched, and if its use is finished, disposed. If the syringe is of a reusable type, the needle subassembly alone may be removed and disposed in the conventional manner, quite independently of the latch mechanism.

If the apparatus is to be used to aspirate a blood sample or other body fluid, the worker simply proceeds to inject the needle 10 into the patient without first filling the syringe, but otherwise in the same manner as for injecting medication, but simply starting with the syringe plunger in extended, rather than retracted position, as is well known in the art. It is noted that the movements and operation of the sheath 24 and latch mechanism are completely independent of the movements of the syringe plunger.

Numerous variations on the exemplary embodiment may be made within the skill of the art and within the scope of this invention, and it is intended that the scope of the invention be limited only by the claims. By way of example only, while the exemplary embodiment shows the flange 18 as an integral part of the fitting of a needle subassembly, it would be possible to make embodiments of the invention in which the base member of the safety mechanism is attached to the syringe, rather than to the needle subassembly. There are, however, advantages to mounting the safety mechanism on the needle subassembly, for example if it is desired to remove and dispose of the needle subassembly and reuse the syringe. In this regard, it is noted that the nature of the latching mechanism is such that the additional length added to a needle subassembly to incorporate the present invention is de minimus.

It is also possible to make embodiments of safety mechanism which can be separately manufactured and subsequently applied by a worker either to the needle subassembly or to the syringe.

Other types of mechanisms for releasably holding the latch device in its free or latched mode, other than snaps 42, could be provided. Also, means other than plate 46 could be used to hold the latch operator in place on the apparatus. In some embodiments, it might be possible to have the latch operator carried on the base member, rather than on the sheath member.

Numerous other modifications are possible.

Additionally, it is noted that, in the claims, references to connections, interconnections, and cooperations between elements are intended to be generally construed; for example, a member may be "cooperative with" or "connected to" another member either directly or indirectly via one or more intervening members, unless specific limiting language, such as "directly,", is included in the claim.

What is claimed is:

1. A safety mechanism for a hypodermic needle comprising:
    a base member adapted to be fixed with respect to the needle;
    a tubular sheath member mounted for relative longitudinal reciprocation with respect to the base member between a first position for covering the needle and a second position wherein the needle can at least partially protrude from an outer end of the sheath member;
    and latch means cooperative between the base member and the sheath and selectively repeatedly shiftable between a latching mode, wherein the sheath member is latched in its first position, and a free mode, wherein the sheath member is so reciprocable between its first and second positions, the latch means including detent means for releasably holding the latch means in its free mode.

2. The apparatus of claim 1 further comprising a spring cooperative between the base and sheath members to bias the sheath member to its first position, and stop means cooperative between the base and sheath members to limit movement of the sheath member toward its first position.

3. The apparatus of claim 2 wherein the detent means is further operative to releasably retain the latch means in its latching mode.

4. The apparatus of claim 3 wherein the detent means comprises resilient snap means which disengage as the latch means is forcibly shifted from either one to the other of its modes and automatically engagable after the latch means reaches such other mode.

5. The apparatus of claim 3 wherein the latch means comprises a latch operator moveable in a circumferential sense with respect to at least one of the base or sheath members to so shift the latch means.

6. The apparatus of claim 5 wherein the latch operator and said one member have respective abutment surfaces circumferentially aligned and axially opposed in the latching mode and circumferentially offset in the free mode.

7. The apparatus of claim 6 wherein the latch operator is mounted on the other of said base or sheath members for such circumferential movement with respect to both said base and sheath members.

8. The apparatus of claim 7 further comprising means cooperative between the base and sheath members to prevent relative rotation of those members.

9. The apparatus of claim 7 wherein said one member is the base member and said other member is the sheath member.

10. The apparatus of claim 9 wherein the base member comprises a flange extending radially outwardly from a fitting mounting the needle and connectable to a syringe, the sheath member being sized to externally surround and reciprocate over the flange and the fitting.

11. The apparatus of claim 10 wherein the sheath member is sized to externally surround and reciprocate over a syringe of a predetermined size.

12. The apparatus of claim 10 wherein the longitudinal dimension of the flange is substantially less than the length of the needle.

13. The apparatus of claim 10 wherein the flange has a radially outwardly opening notch, and the latch operator has a radially inward projection sized to fit in the notch, circumferentially offset from the notch in the latching mode and circumferentially aligned with the notch in the free mode.

14. The apparatus of claim 10 wherein the sheath member has a slit therethrough elongated in a circumferential direction; and the operator includes an engagement portion externally overlying the sheath member in the vicinity of the slit and from which the radial projection projects through the slit, 15. The apparatus of claim 14 wherein the radial projection includes a longitudinally enlarged retainer portion internally underlying the sheath member in the vicinity of the slit.

16. The apparatus of claim 14 wherein the sheath member has detent snap formation means projecting laterally into the slit and sized and adapted to abut the radial projection of the operator and resist circumferential movement thereof but resiliently yield to permit such circumferential movement upon application of sufficient force, the slit being sized to receive the radial projection of the operator on either side of the snap formation means.

17. The apparatus of claim 14 further comprising two indicia of the sheath member, each respectively covered by the engagement portion of the operator when the latch means is in a respective one of its modes.

18. The apparatus of claim 1 wherein the external surface of the sheath member has a portion tapered inwardly toward its outer end, the tapered portion having surface irregularities.

19. A safety mechanism for a hypodermic needle comprising:
    a base member adapted to be fixed with respect to the needle and comprising a flange extending radially outwardly from a line containing the locus of the centerline of the needle, the flange having a radially outwardly opening notch;
    a tubular sheath member sized to externally surround the base member and mounted for relative longitudinal reciprocation with respect to the base member between a first position for covering the needle and a second position wherein the needle can at least partially protrude from an outer end of the sheath member, the sheath member having a slit therethrough elongated in a circumferential direction, the sheath member also carrying stop means cooperative with the base member for limiting relative longitudinal movement toward the first position;
    a latch operator comprising an engagement portion accessible from the outside of the sheath member, and a projection extending radially inwardly from the engagement portion, through the slit, and sized to fit in the notch in the flange of the base member, the part of the projection disposed in the slit being smaller than the slit in a circumferential sense whereby the latch operator can be moved in a circumferential sense with respect to the sheath member between a latching mode wherein the projection is circumferentially offset from the notch in the flange and is opposed to the flange, and a free mode wherein the projection is circumferentially aligned with the notch.

20. The apparatus of claim 19 further comprising detent means cooperative between the latch operator and the sheath member resisting circumferential movement of the latch operator, but resiliently yieldable to permit such circumferential movement upon application of sufficient force.

21. The apparatus of claim 19 wherein a needle is mounted in the base member, and the base member is adapted for connection to a syringe, the sheath member being sized to externally surround and reciprocate over a syringe of a predetermined size.

22. A safety mechanism for a hypodermic needle comprising:
  a base member adapted to be fixed with respect to the needle;
  a tubular sheath member mounted for relative longitudinal reciprocation with respect to the base member between a first position for covering the needle and a second position wherein the needle can at least partially protrude from an outer end of the sheath member;
  latch means cooperative between the base member and the sheath and selectively repeatedly shiftable between a latching mode, wherein the sheath member is latched in its first position, and a free mode, wherein the sheath member is so reciprocable between its first and second positions; and
  a latch operator accessible from the exterior of the mechanism and movable with respect to both the base member and the sheath member to so shift the latch means.

23. The apparatus of claim 22 wherein the latch means includes detent means for releasably holding the latch means in its free mode.

24. A safety mechanism for a hypodermic needle comprising:
  a base member adapted to be fixed with respect to the needle, the base member comprising a flange extending radially outwardly from a fitting mounting the needle and connectable to a syringe, the flange having a radially outwardly opening notch;
  a tubular sheath member sized to externally surround and reciprocate over the flange and the fitting, and mounted for relative longitudinal reciprocation with respect to the base member between a first position for covering the needle and a second position wherein the needle can at least partially protrude from an outer end of the sheath member, the sheath member having a slit therethrough elongated in a circumferential direction;
  latch means cooperative between the base member and the sheath and selectively repeatedly shiftable between a latching mode, wherein the sheath member is latched in its first position, and a free mode, wherein the sheath member is so reciprocable between its first and second positions, the latch means comprising a latch operator mounted on the sheath member and moveable in a circumferential sense with respect to the base member and the sheath member, the latch operator having a radially inward projection sized to fit in the notch of the flange of the base member, circumferentially offset from the notch and abuttable with the flange in the latching mode, and circumferentially aligned with the notch in the free mode, and further comprising an engagement portion externally overlying the sheath member in the vicinity of the slit and from which the radial projection projects through the slit.

* * * * *